US012765869B2

(12) United States Patent
Jones et al.

(10) Patent No.: US 12,765,869 B2
(45) Date of Patent: Oct. 20, 2026

(54) MOLDABLE JAMMING GRIP FOR SURGICAL INSTRUMENTS

(71) Applicant: Arthrex, Inc., Naples, FL (US)

(72) Inventors: Chad Jones, Naples, FL (US); Stephen Seipel, Naples, FL (US)

(73) Assignee: Arthrex, Inc., Naples, FL (US)

(*) Notice: Subject to any disclaimer, the term of this patent is extended or adjusted under 35 U.S.C. 154(b) by 235 days.

(21) Appl. No.: 18/526,116

(22) Filed: Dec. 1, 2023

(65) Prior Publication Data

US 2024/0180536 A1 Jun. 6, 2024

Related U.S. Application Data

(60) Provisional application No. 63/430,166, filed on Dec. 5, 2022.

(51) Int. Cl.
*A61B 17/00* (2006.01)

(52) U.S. Cl.
CPC .... *A61B 17/00* (2013.01); *A61B 2017/00398* (2013.01); *A61B 2017/0042* (2013.01); *A61B 2017/0046* (2013.01)

(58) Field of Classification Search
CPC ... B25G 1/00; B25G 1/01; B25G 1/02; B25G 1/10; B25G 1/102; A61B 2017/00398; A61B 2017/0042; A61B 2017/0046; A61B 2017/00424; A61B 17/00
See application file for complete search history.

(56) References Cited

U.S. PATENT DOCUMENTS

| | | | | |
|---|---|---|---|---|
| 4,765,856 | A | 8/1988 | Doubt | |
| 5,155,878 | A | 10/1992 | Dellis | |
| 6,148,483 | A * | 11/2000 | DeGraff | A63B 59/50 16/431 |
| 7,294,110 | B2 * | 11/2007 | Bourne | B25F 5/006 600/564 |
| 9,448,066 | B2 | 9/2016 | Follmer et al. | |
| 9,764,220 | B2 | 9/2017 | Keating et al. | |
| 9,777,753 | B2 | 10/2017 | Niiyama et al. | |
| 9,812,100 | B1 | 11/2017 | Mobley | |
| 10,434,618 | B2 | 10/2019 | Corrigan et al. | |
| 10,538,049 | B2 | 1/2020 | Corrigan et al. | |

(Continued)

FOREIGN PATENT DOCUMENTS

| | | | | |
|---|---|---|---|---|
| DE | 102020133207 | A1 | 6/2022 | |
| GB | 2493147 | A * | 1/2013 | B25G 1/102 |

(Continued)

OTHER PUBLICATIONS

Follmer et al., "Jamming User Interfaces: Programmable Particle Stiffness and Sensing for Malleable and Shape-Changing Devices," Oct. 7, 2012, https://dl.acm.org/doi/10.1145/2380116.2380181.

*Primary Examiner* — Brian T Gedeon
(74) *Attorney, Agent, or Firm* — Price Heneveld LLP

(57) ABSTRACT

A surgical device includes a support member forming a connection interface extending from a portion of the surgical device. A moldable handle includes an interior liner extending over at least a portion of the connection interface and an exterior engagement layer in connection with the interior liner defining a grip surface. The interior liner and the exterior engagement layer form an enclosed cavity therebetween. A jamming material is disposed in the enclosed cavity.

18 Claims, 9 Drawing Sheets

(56) References Cited

U.S. PATENT DOCUMENTS

| | | | |
|---|---|---|---|
| 10,828,178 | B2 | 11/2020 | Hill et al. |
| 10,828,450 | B2 | 11/2020 | Scheirlinck et al. |
| 10,864,104 | B2 | 12/2020 | Corrigan et al. |
| 10,881,763 | B2 | 1/2021 | Kim et al. |
| 11,364,139 | B2 | 6/2022 | Chang et al. |
| 2016/0106508 | A1 | 4/2016 | Lathrop et al. |
| 2019/0314112 | A1 | 10/2019 | Wellborn et al. |

FOREIGN PATENT DOCUMENTS

| | | | |
|---|---|---|---|
| JP | 2007029249 | A | 2/2007 |
| KR | 20140110320 | A | 9/2014 |

* cited by examiner

MOLDABLE JAMMING GRIP FOR SURGICAL INSTRUMENTS

CROSS-REFERENCE TO RELATED APPLICATIONS

This application claims priority under 35 U.S.C. § 119(e) and the benefit of U.S. Provisional Application No. 63/430,166 entitled MOLDABLE JAMMING GRIP FOR SURGICAL INSTRUMENTS, filed on Dec. 5, 2022, by Jones et al., the entire disclosure of which is incorporated herein by reference.

BACKGROUND

The present disclosure generally relates to interfaces or grips associated with surgical instruments and tools and, more particularly, to moldable handles for surgical devices and tools that are selectively formed to provide rigid, custom contours. Tools associated with surgical operations may vary widely depending on their intended applications and the preferences of the users (e.g., physicians, surgeons, medical staff, etc.). In addition to the variety of the instruments and tools applied in surgical procedures, each user may also apply different gripping styles and techniques to complete the procedures. In various implementations, the disclosure may provide for apparatuses and corresponding methods to facilitate the use of instruments and tools to accomplish a variety of surgical procedures.

SUMMARY

Surgical implements (e.g., devices, tools, instruments, etc.) may incorporate a variety of user interfaces or engagement structures in the form of handles or grips to accommodate a wide variety of surgical procedures. In addition to the requirement of the surgical implements to accomplish each procedure, the implements may also vary to fulfill various preferences and techniques that may vary among surgeons and medical professionals. However, user preferences and styles may be so numerous and/or specific that customization may become impractical. In various implementations, the disclosure provides for a moldable handle or gripping apparatus that may be implemented in a wide variety of surgical devices and molded to suit the specific preferences of each user through a simple customization procedure.

In various implementations, the disclosure provides for a moldable grip or handle that may be selectively connected to a support member or handle body in connection with a portion of a surgical device. In order to provide for the customization of the moldable grip, a jamming material may be disposed within an enclosed cavity formed between an interior liner and an exterior engagement layer. The interior liner may be configured and/or proportioned to receive the handle body or a connection interface of the surgical device. The exterior engagement layer may define a grip surface extending over and conforming to the jamming material disposed within the enclosed cavity. In this configuration, the jamming material may be adjusted between a jammed condition and a flexible condition in response to a variation in pressure within the enclosed cavity. The variation and pressure within the enclosed cavity may be the result of a pressure differential between the jamming material and a local environment that may be varied by adjusting an air pressure within the enclosed cavity via a pump or suction device. In this way, the disclosure may provide for the customization of one or more contours formed by the jamming material of the moldable grip to facilitate a wide variety of gripping or engagement preferences for the surgical device.

In various implementations, the moldable grip may correspond to a handle portion that may be removable from the handle body via a slideable engagement between the handle body and the interior liner. In such configurations, the moldable grip and handle portion may correspond to interchangeable components that may be selectively attached to the surgical device to vary the moldable grip between surgical procedures. Accordingly, the handle portion and moldable grip may correspond to disposable devices or removable devices that may be sanitized and treated separately from the surgical device between surgical procedures. In various implementations, the moldable grip and handle portion may be implemented as an interchangeable or removable accessory or a permanently affixed component of a surgical device, depending on the preferred application. In order to more clearly understand the nature of the moldable grip and corresponding features provided by the disclosure, a variety of examples are provided in the following detailed description.

These and other features, objects and advantages of the present disclosure will become apparent upon reading the following description thereof together with reference to the accompanying drawings.

DETAILED DESCRIPTION

In the following description, reference is made to the accompanying drawings, which show specific implementations that may be practiced. Wherever possible, the same reference numbers will be used throughout the drawings to refer to the same or like parts. It is to be understood that other implementations may be utilized and structural and functional changes may be made without departing from the scope of this disclosure.

Figure 1:
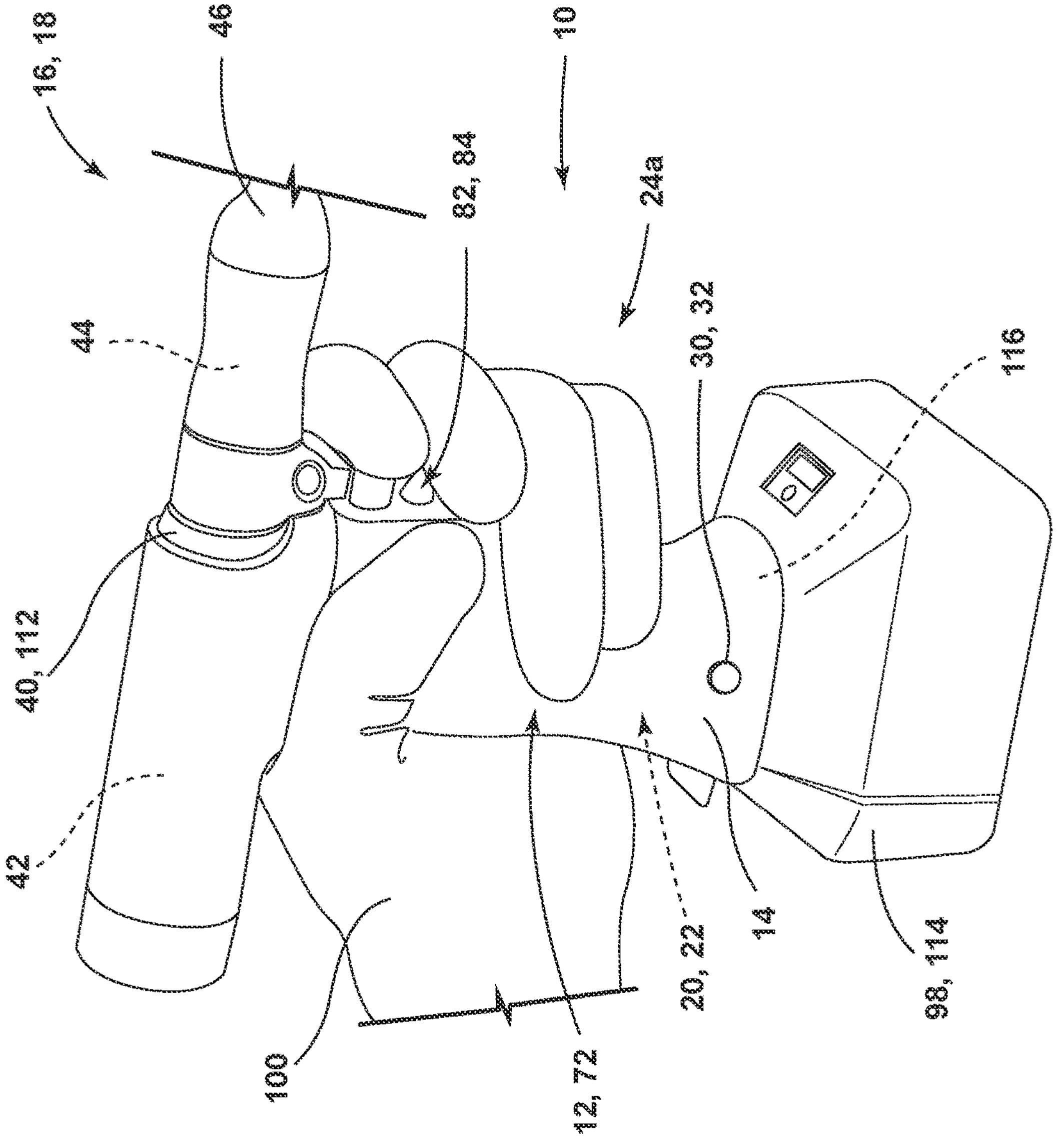
FIG. 1 is a projected view of a surgical device comprising a moldable grip.
Figure 2A:
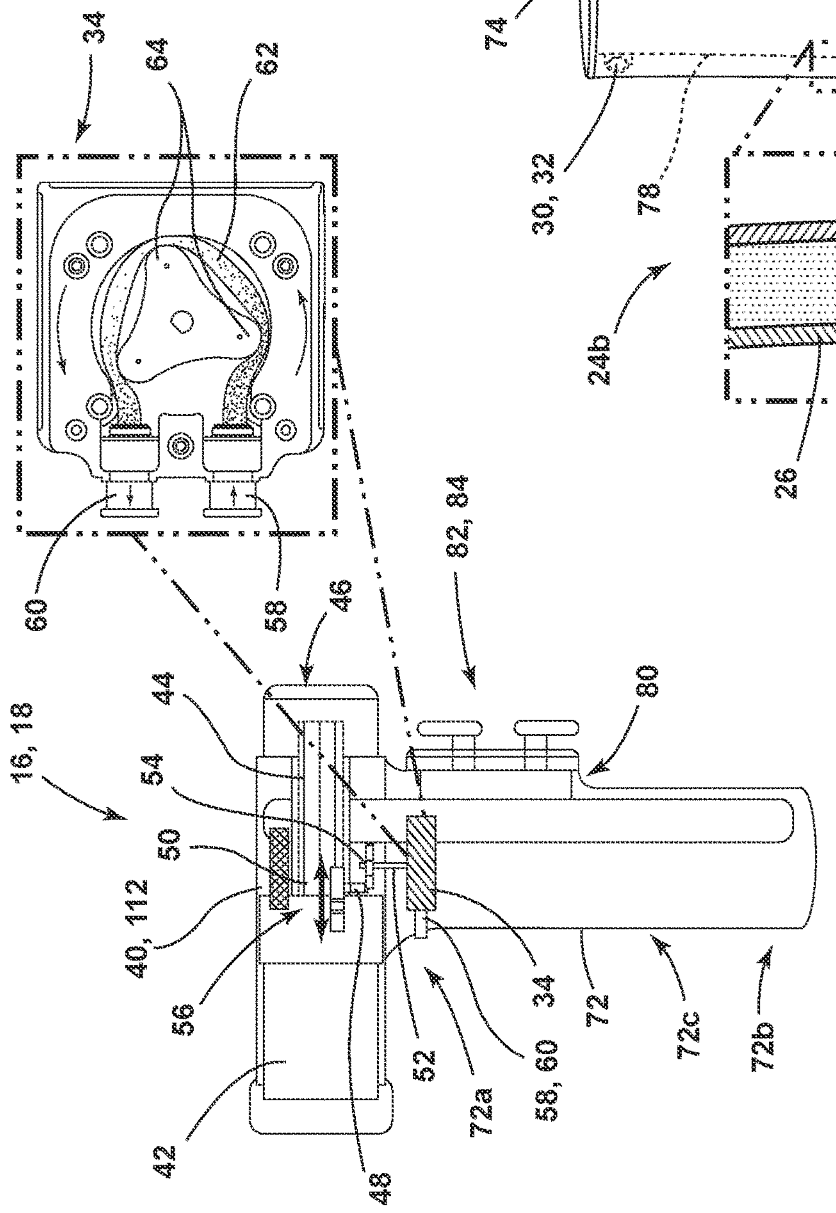
FIG. 2A is a schematic diagram demonstrating a side view of a surgical device compatible with a handle portion comprising a moldable grip.
Figure 2B:
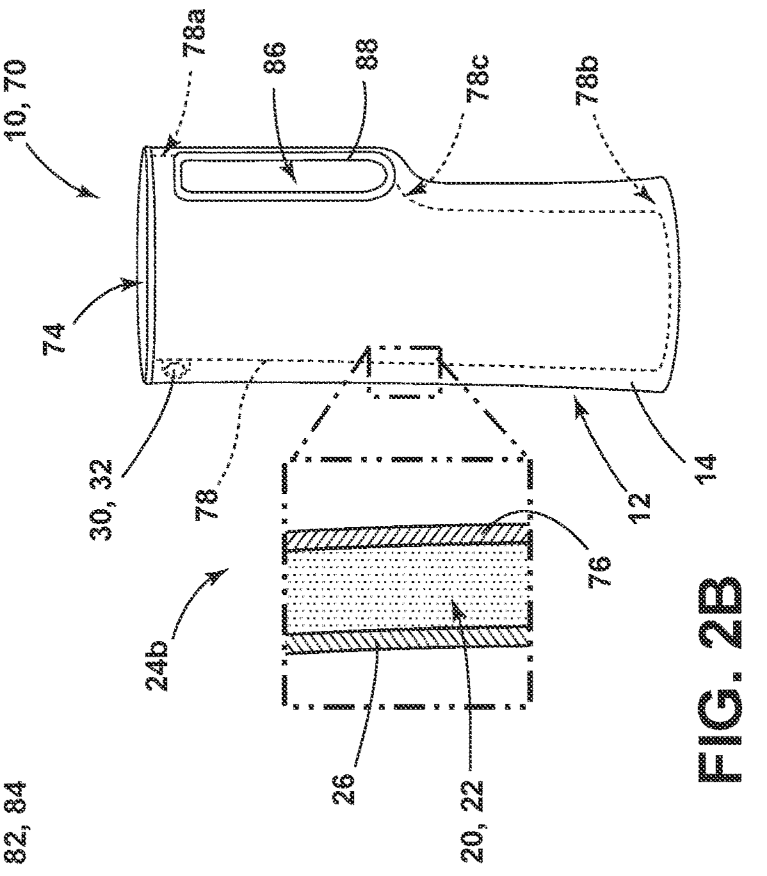
FIG. 2B is a schematic diagram demonstrating a handle portion comprising a moldable grip compatible with the surgical device demonstrated in FIG. 2A.

Referring to FIGS. 1, 2A and 2B, the disclosure may generally provide for a handle apparatus 10, which may correspond to a customizable handle portion 12 comprising a moldable grip 14 that may be formed to suit a variety of gripping positions associated with a surgical device 16. In some implementations, the moldable grip may provide for the customization of various surface contours and/or gripping features formed by the selective molding of a jamming material or media, disposed within an enclosed cavity 22 of the moldable grip 14. As later discussed in various examples throughout the following description, the jamming material may be adjusted between a jammed condition 24*a* and a flexible condition 24*b* in order to selectively mold the grip 14 into various shapes that may vary to suit a gripping preference, hand size, procedural technique, or various preferences that may be associated with the use of the surgical device 16. As described in reference to a variety of specific examples of the surgical device 16 as well as handheld tools 130, the handle apparatus 10 may generally be applied to a variety of surgical implements 18. Accordingly, the disclosure may provide for the moldable grip 14 and corresponding methods to facilitate the customization of a wide variety of surgical implements 18 to suit the needs and preferences of surgeons and medical professionals.

As discussed herein, the jamming material 20 or jamming media may correspond to a granular substance having a particulate structure that forms interstitial spaces among the particles forming its cumulative structure. In operation, the jamming material 20 may be adjusted from the jammed condition 24*a* to the flexible condition 24*b* by adjusting a pressure or vacuum pressure within the enclosed cavity 22 formed by the moldable grip 14. In this configuration, the pressure within the enclosed cavity 22 may be increased, such that the particles forming the jamming material 20 easily shift and move relative to each other and conform to external forces applied to an external engagement layer 26 of the moldable grip 14. When the pressure is withdrawn or the air is evacuated from within the enclosed cavity 22, the particles forming the jamming material 20 may effectively be fused as the result of the corresponding interstitial spaces between the particles being compressed by the engagement layer 26. The compression of the particles forming the jamming material 20 may positionally bind the particles relative to one another within the enclosed cavity 22 and create a rigid structure. In this way, the moldable grip 14 may be molded, released, and remolded to provide a custom grip structure.

The pressure within the enclosed cavity 22 may be adjusted via a valve 30 that may control the passage of air or fluid through an aperture 32 formed through the moldable grip 14 and fluidically connected to the enclosed cavity 22. In this configuration, a pump 34 (e.g., a pneumatic pump, peristaltic pump, etc.) may be selectively activated in connection with the valve 30 to adjust the pressure within the enclosed cavity 22 and transition the jamming material 20 from the jammed condition 24*a* to the flexible condition 24*b* and vice versa. In some cases, the pump 34 or a pressure regulation device may be incorporated as a part of the assembly of the surgical tool. In each implementation, the adjustment of the pressure within the enclosed cavity 22 may provide for repeated and flexible customization of the moldable grip 14 to support a wide variety of applications.

As demonstrated in FIG. 2A, the pump 34 may be incorporated within a tool housing 40 of the surgical device 16. In such implementations, the pump 34 may be driven by a dedicated motor and/or a drive motor 42 associated with the operation of the surgical device 16. For example, in cases where the surgical implement 18 or device 16 corresponds to a surgical power tool, the drive motor 42 may be configured to drive an output shaft 44 that may be in connection with a chuck 46 configured to connect to a variety of surgical cutting tools or similar implements. In implementations where the pump 34 is driven by the drive motor 42, a sprocket 48 that rotates in coordination with a drive hub 50 of the output shaft 44 may be selectively engaged with a pump drive axle 52 in connection with a decoupling gear 54. In operation, the decoupling gear 54 may be selectively engaged and disengaged with the sprocket 48 in response to a position of an actuation switch 56, demonstrated in connection with tool housing 40. In this way, the actuation switch 56 may be selectively positioned to engage or disengage the decoupling gear 54, such that the drive motor 42 may selectively control a rotation as well as a direction of fluid flow controlled via the pump 34.

FIG. 2A demonstrates a detailed sectional view of an exemplary peristaltic implementation of the pump 34. As shown, the pump 34 comprises an inlet 58 and an outlet 60 in connection with a hose 62. A plurality of rollers 64 are connected to the pump drive axle 52. In this configuration, the activation of the drive motor 42 when engaged with the decoupling gear 54 may result in a corresponding rotation of the pump drive axle 52, thereby controlling the rotation of the roller 64 and corresponding operation of the pump 34. The bidirectional rotational operation of the drive motor 42 may, therefore, provide for the supply or suction of the air within the enclosed cavity 22 to selectively adjust the jamming material 20 from the jammed condition 24*a* to the flexible condition 24*b* and vice versa. Though the peristaltic pump is demonstrated in the example shown in FIG. 2A, it shall be understood that various pumping or air suction technologies may be implemented to support the operation discussed in reference to the moldable grip 14.

Referring now to FIG. 2B, the moldable grip 14 may correspond to a sleeve 70 that may be detachably mounted to a handle body 72 or connection post rigidly connected to the surgical device 16. In this configuration, the moldable grip 14 may slidably engage over the handle body 72, such that at least a portion of the handle body 72 extends into a receiving opening 74 formed by an interior liner 76 of the moldable grip 14. Depending on the specific application, the interior liner 76 may correspond to a rigid material and/or a flexible material that may conform to one or more contours of the handle body 72 for support posts connected to the surgical device 16.

As further demonstrated in FIG. 2B, the sleeve 70 or jacket may include one or more features that conform to or otherwise accommodate the proportions of the handle body 72. For example, the handle body 72 may extend from a proximal handle portion 72*a* in connection with the tool housing 40, or more generally the tool, to a distal handle portion 72*b* extending away from the tool housing 40. As depicted, the sleeve 70 or jacket forming the receiving opening 74 of the moldable grip 14 may comprise a contoured interior profile 78 that conforms to corresponding handle contours 80 of the handle body 72. For example, the contoured interior profile 78 may extend from a first interior cross section 78*a* to a second interior cross section 78*b* with a contoured transition 78*c* therebetween. The contoured interior profile 78 may be formed by the corresponding proportions of the interior liner 76 to accommodate the proportions of the handle body 72.

As shown, the first interior cross section 78*a* may proportion the receiving opening 74 to receive the proximal handle portion 72*a* of the handle body. The second interior cross section 78*b* may have a smaller interior cross-sectional area that conforms to the distal handle portion 72*b*. Additionally, the contoured transition 78*c* may correspond to and accommodate a portion of the handle body 72 that changes in cross section proximal to a user interface 82, demonstrated in the form of a trigger assembly 84. In order to accommodate the user interface 82, the moldable grip 14 may further comprise an interface opening formed through the interior liner 76 and the engagement layer 26 to accommodate the proportions of the user interface 82 that may be exposed outside the moldable grip 14. As shown, the interface opening 86 may comprise a perimeter edge 88 that conforms to a surface perimeter extending about the user interface 82. In this configuration, the interior liner 76 of the moldable grip 14 may conform to the handle contours 80 of the handle body 72 and provide for an exterior moldable wall that closely fits the handle body 72 in an assembled configuration. Though discussed in reference to the specific sample depicted in FIGS. 1 and 2A-2B, the contoured interior profile 78 and interface opening 86 may conform to various features associated with the handle body 72 of a variety of surgical devices 16 and/or implements.

Figure 3A:
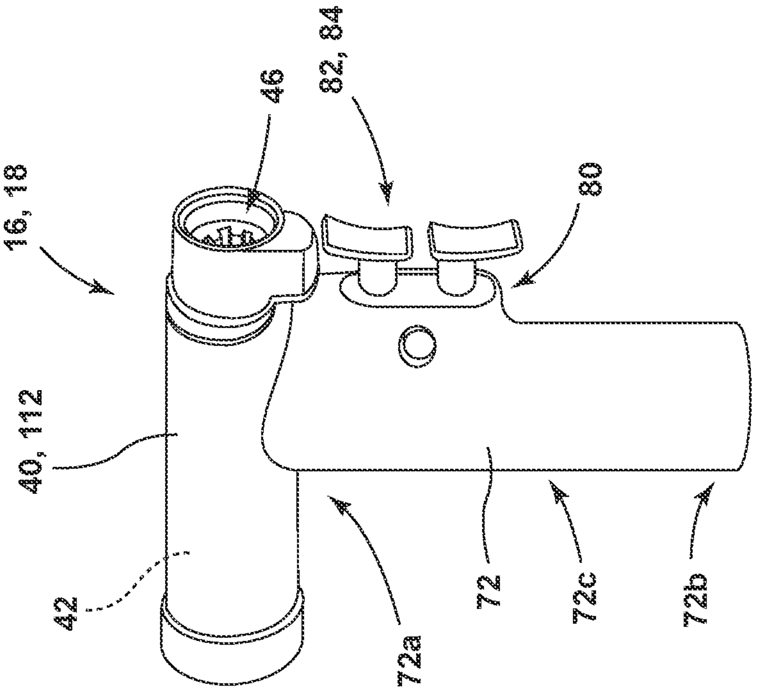
FIG. 3A is a schematic diagram demonstrating a side view of a surgical device compatible with a handle portion comprising a moldable grip.
Figure 3B:
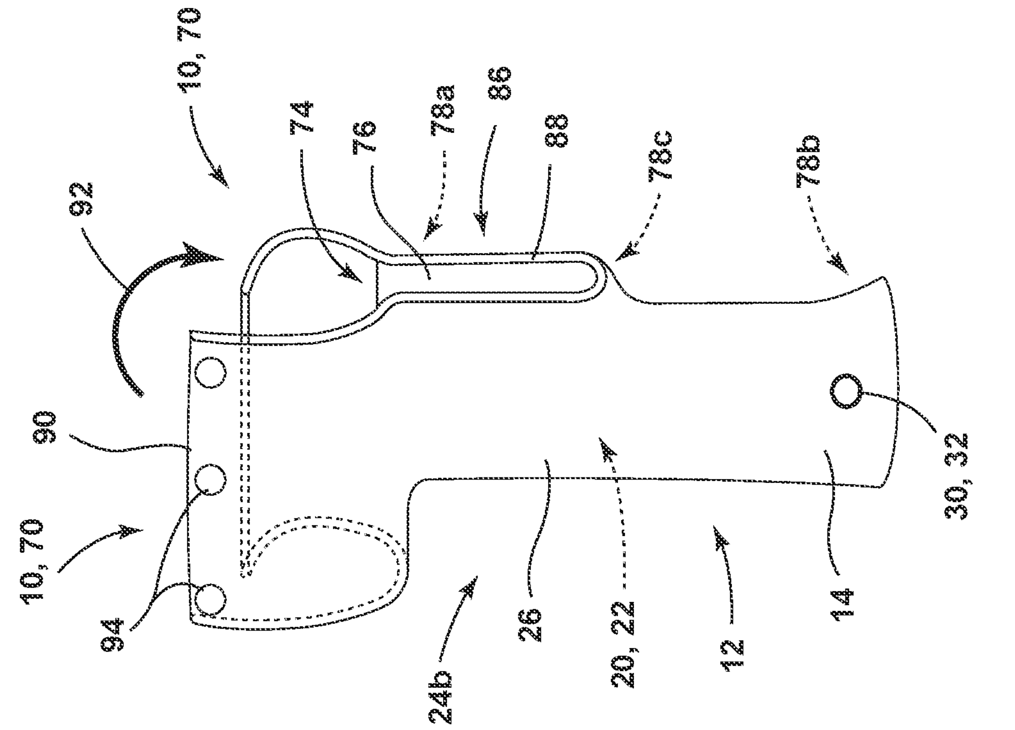
FIG. 3B is a schematic diagram demonstrating handle portion comprising a moldable grip compatible with the surgical device demonstrated in FIG. 3A.

Referring now to FIGS. 3A-3D, an exemplary implementation of the handle apparatus 10 is shown in reference to the surgical device 16 and the moldable grip 14 comprising a releasable closure 90. As shown in FIG. 3A, the surgical device 16 is similar to the example discussed in reference to FIGS. 1 and 2A-2B, and may further demonstrate the releasable closure 90 providing a wraparound feature 92 configured to connect to the perimeter of the receiving opening 74. The releasable closure 90 may form a snap-closure comprising a plurality of fasteners 94 (e.g., buttons). In this configuration, the handle portion 12 formed by the moldable grip 14 may slidably engage the handle body 72 and be secured to the surgical device 16 by enclosing the releasable closure 90 about the tool housing 40.

During assembly, the interface opening 86 may receive the user interface 82 or trigger assembly 84, thereby positioning the perimeter edge 88 of the interface opening 86 about the trigger assembly 84. Once the fasteners 94 of the releasable closure 90 are secured about the tool housing 40, the moldable grip 14 may be secured and ready for forming the jamming material 20 to customize one or more surface contours of the moldable grip 14. Referring now to FIG. 3C, a hand 100 of a user is shown engaging the engagement layer 26 of the moldable grip 14. The hand 100 demonstrated in the instant example is a left hand that may apply an external force to the engagement layer 26, causing the jamming material 20 to conform to the contours of the hand 100 in the flexible condition 24*b*. Additionally, it shall be understood that the handedness (e.g., a right handedness) of the moldable grip 14 may be molded in the flexible condition 24*b* to conform to a different dexterity and/or a different grip style (e.g., a first grip, a digital pronate grip, a pincer grip, a pencil grip, etc.). Accordingly, the disclosure may provide for the moldable grip 14 to be selectively customized to suit a variety of gripping or interface preferences of a user.

Figure 3D:
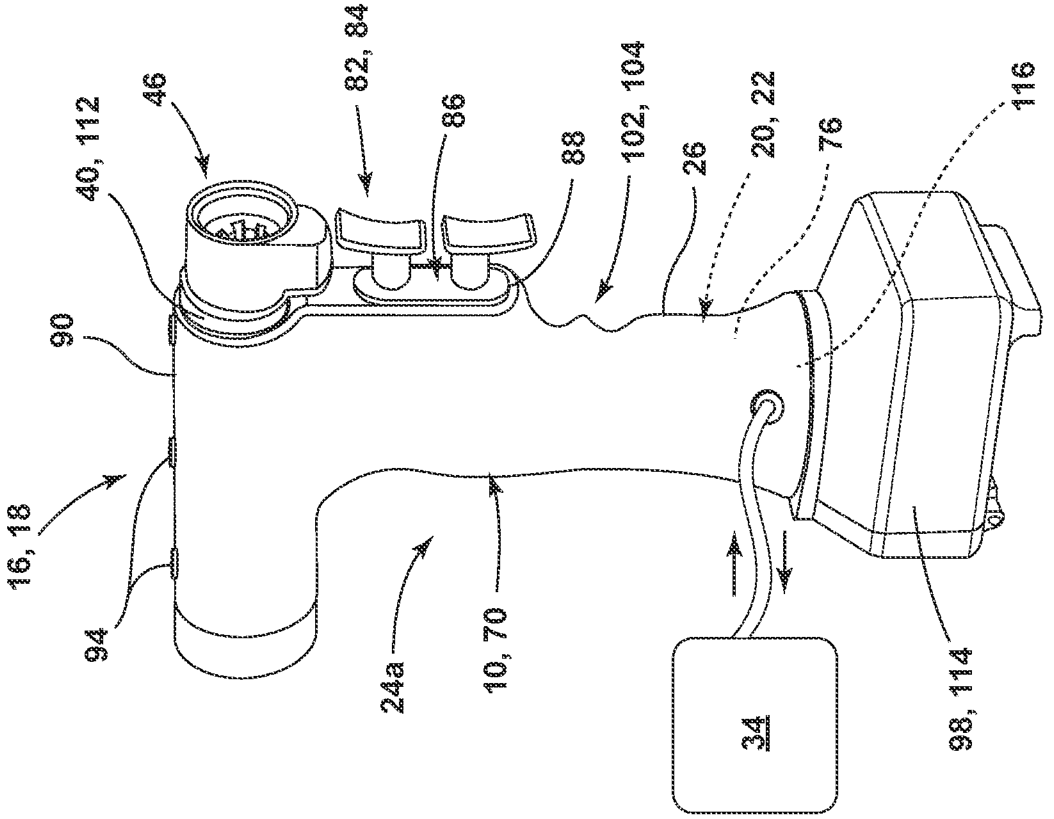
FIG. 3D is a projected view demonstrating a customized contour shape resulting from the molding process demonstrated in FIG. 3C.
Figure 3C:
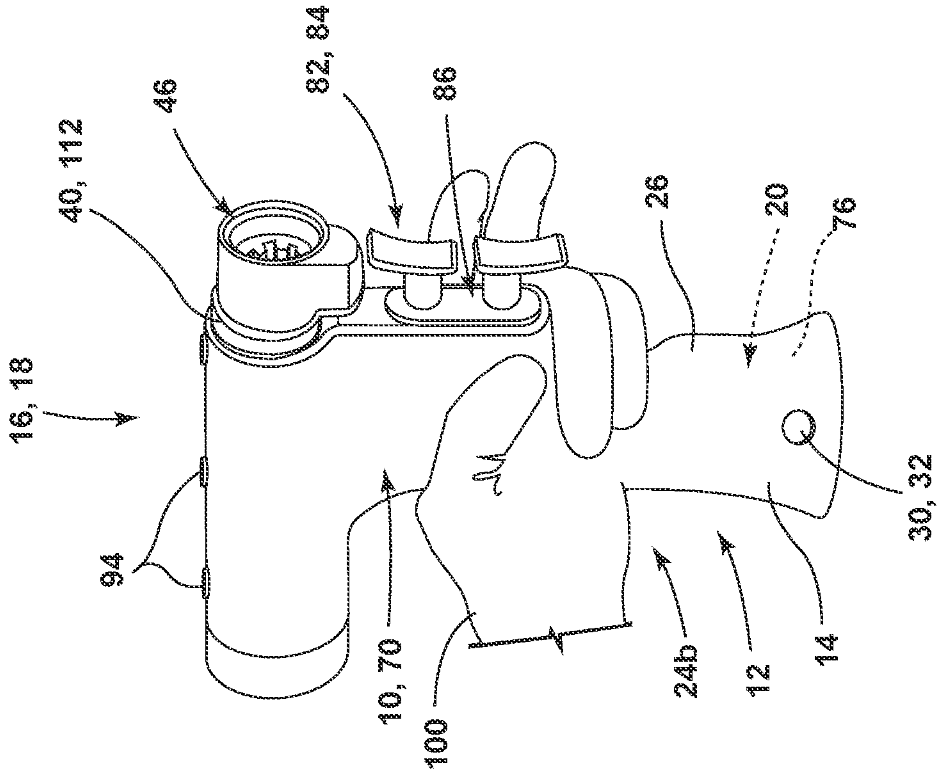
FIG. 3C is a illustrative view of a forming operation of a jamming material for a moldable grip.

As shown in FIG. 3D, the moldable grip 14 may be formed to include an exterior contoured profile 102 corresponding to an impression left by the hand 100 in the jamming material 20 in the flexible condition 24*b*. Once the exterior contoured profile 102 is defined by the user, the pump 34 may be placed in fluid communication with the enclosed cavity 22 via the valve 30 and the valve aperture 32. The pump 34 may then be activated to evacuate air from within the enclosed cavity 22, thereby transitioning the jamming material 20 to the jammed condition 24*a*. As previously discussed, the jamming material 20 in the jammed condition 24*a* may be bound, providing a rigid structural form extending over the handle body 72, thereby providing a customized user engagement interface 104 of the handle portion 12. Once the moldable grip 14 is formed in the jammed condition 24*a*, a battery pack 98 may be connected to the handle body 72 to facilitate use of the surgical device 16 in a powered configuration.

Following the desired use of the surgical device 16, the pump 34 may similarly be implemented to release the jamming material 20 to the flexible condition 24*b* by supplying air pressure into the enclosed cavity 22 via the valve 30 and valve aperture 32. In this way, the moldable grip 14 may be repeatedly customized, providing different exterior contoured profiles 102 and corresponding customized engagement interface 104 to facilitate the handedness and/or gripping style of a variety of users of the surgical devices 16. Though discussed in reference to the powered surgical device 16 or power tool and demonstrated in later examples, the handle portion 12 and moldable grip 14 may be implemented with a variety of surgical implements 18.

Figure 4B:
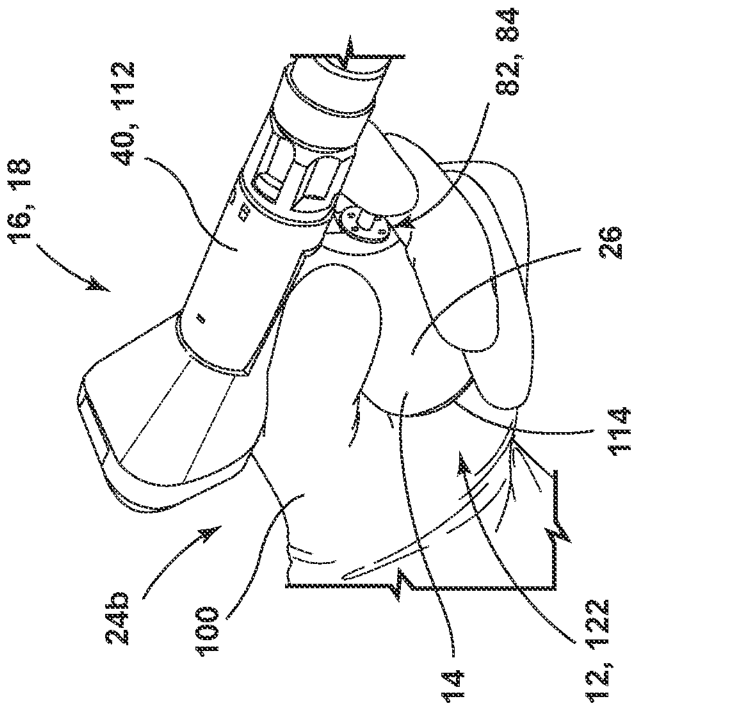
FIG. 4B is a pictorial representation of a molding operation of the moldable grip shown in FIG. 4A.
Figure 4A:
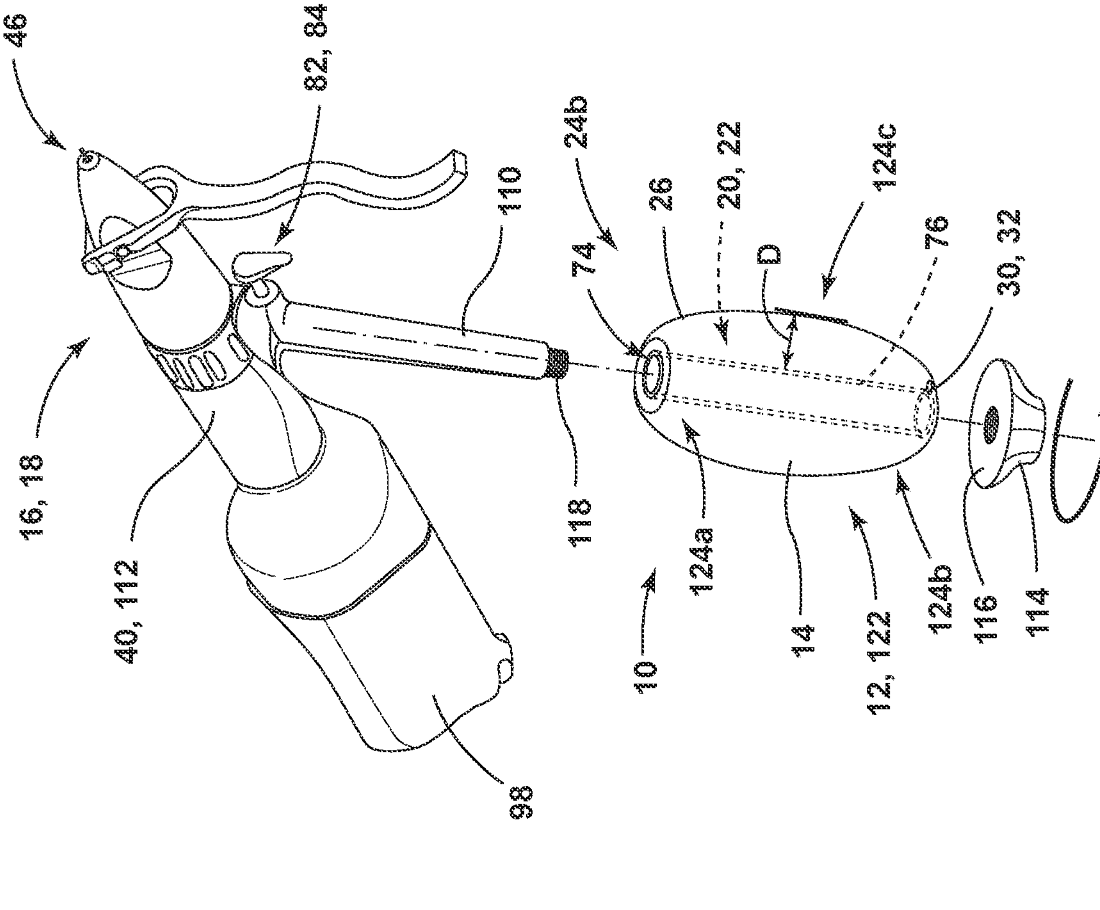
FIG. 4A is an exploded assembly view of a surgical device demonstrating a handle portion comprising a moldable grip.

Referring now to FIGS. 4A-4D, an example of the surgical device 16 is shown demonstrating a structural support post 110 in connection with a tool body 112 and configured to receive the handle portion 12 comprising the moldable grip 14. As depicted, the support post 110 may be implemented similar to the handle body 72 and provide a structural support and/or connection to the housing 40 or the body 112 of the implement 18. As shown in FIG. 4A, the receiving opening 74 of the interior liner 76 may be configured to receive a length of the support post 110 passing through a corresponding length of the moldable grip 14. The moldable grip 14 may then be secured to the surgical device 16 and the support post 110 via a retaining feature 114 (e.g., a threaded or latching fastener or tab) comprising a retaining plate 116 forming a retaining surface. In the example shown, the retaining feature 114 may be affixed to the support post 110 via a threaded connection 118. In this configuration, the retaining feature 114 may be positioned such that the retaining plate 116 or retaining surface secures the handle portion 12 comprising the moldable grip 14 to the support post 110.

Figure 4C:
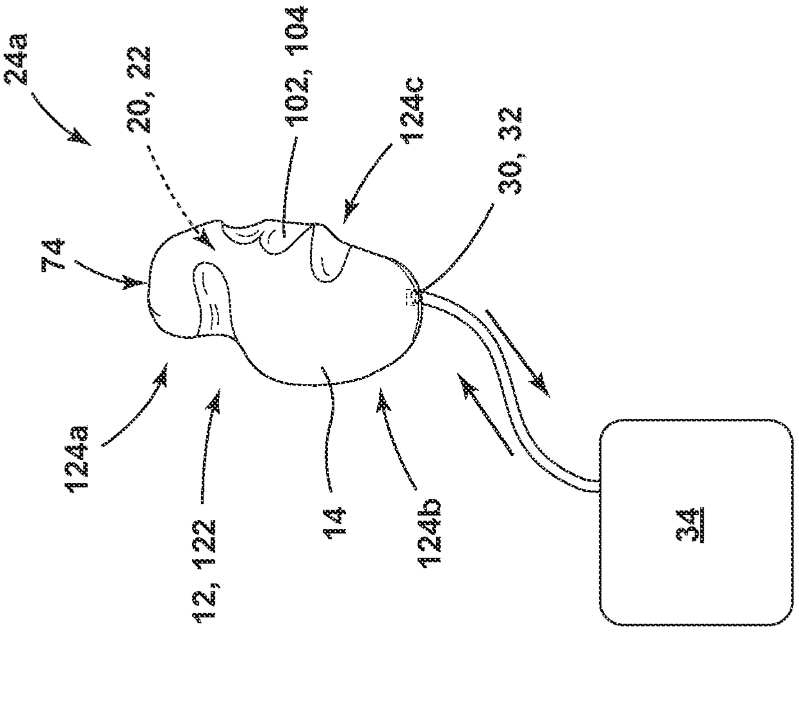
FIG. 4C is a schematic representation of a transitioning process of a jamming material of the moldable grip demonstrated in FIG. 4B adjusted from a flexible condition to a jammed condition.
Figure 4D:
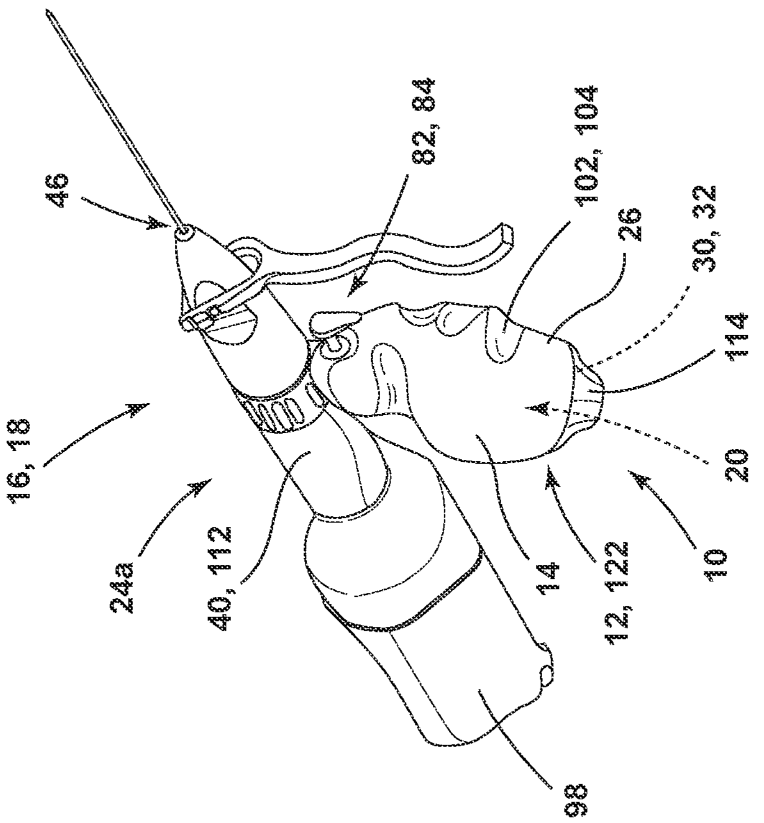
FIG. 4D is a pictorial representation of the moldable grip of FIGS. 4A-4C demonstrated in a custom molded, jammed configuration.

Once the handle portion 12 is secured to the support post 110, the moldable grip 14 may similarly be molded in the flexible condition 24*b* to the hand 100 to suit a handedness, dexterity, and/or grip style of a user. As shown in FIG. 4C, the handle portion 12 and moldable grip 14 are shown isolated from the surgical device 16 to demonstrate the detail of the exterior contour profile 102 and corresponding customized engagement interface 104 to which the jamming material 20 is formed. Once formed, the jamming material 20 may be transitioned from the flexible condition 24*b* to the jammed condition 24*a* by adjusting the pressure within the enclosed cavity 22 via the pump 34, as previously discussed. With the customized engagement interface 104 rigidly affixed into the external engagement surface 26 defined by the jamming material 20, the surgical device 16 may be manipulated via moldable grip 14 and applied in a procedure. Following use of the surgical device 16, the jamming material 20 may be returned to the flexible condition 24*b*, such that the contoured profile 102 may be adjusted and/or reshaped to create a new and different customized engagement interface 104.

In addition to the features discussed in reference to the support posts 110, the handle portion 12 and moldable grip 14 demonstrated in FIGS. 4A-4D may further demonstrate the jamming material 20 formed in an elliptical or ovate shape 122. As demonstrated in FIG. 4A, the ovate shape 122 may extend outward between a proximal handle portion 124*a* and a distal handle portion 124*b* to a bulbous central portion 124*c* therebetween. In this configuration, a thickness of the jamming material 20 between the engagement layer 26 and the interior liner 76 may increase between the proximal handle portion 124*a* and the distal handle portion 124*b* to form the bulbous central portion 124*c*. Accordingly, a molding depth D of the jamming material 20 may be unevenly distributed along the length of the moldable grip 14 and maximized at the bulbous central portion 124*c*. Varying the molding depth D along the length of the handle portion 12 may allow the moldable grip 14 to conform to a wide variety of gripping styles to accommodate various user preferences of the surgical device 16.

Though demonstrated with the molding depth D increased centrally along the length of the handle portion 12, it shall be understood that the moldable grip 14 may similarly comprise a number of variations. For example, the moldable grip 14 may comprise a bulbous proximal handle portion 124*a* with a narrow distal handle portion 124*b*. The moldable grip may also comprise opposing bulbous proximal and distal handle portions 124*a*, 124*b* with a narrow central portion 124*c* therebetween. In some examples, the grip 14 may comprise a narrow proximal portion 124*a* with a bulbous distal handle portion 124*b* or any variety of combinations of proportions of the jamming material 20, which may be accommodated by the dimensions of the external engagement layer 26 relative to the interior liner 76 to define the molding depth D along the length of the moldable grip 14. Accordingly, the handle portion 12 and moldable grip 14 may be customized to suit a wide variety of applications for use with various surgical devices 16 and implements 18.

Figure 5B:
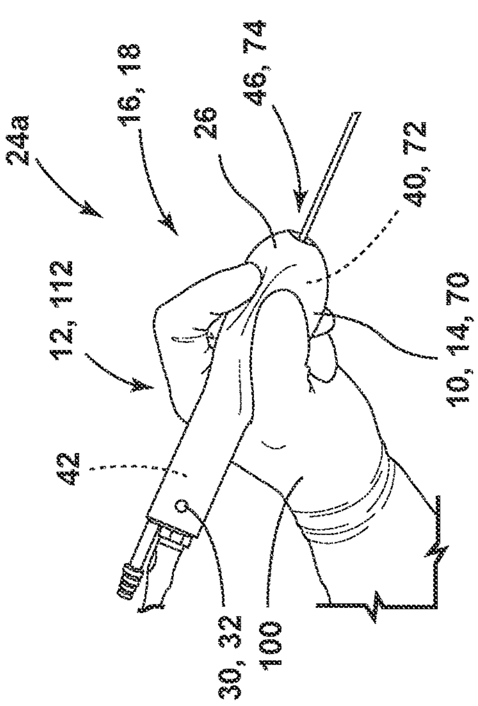
FIG. 5B is a pictorial view of a surgical device implemented via a tripod or pencil-grip having a left-handedness.
Figure 5C:
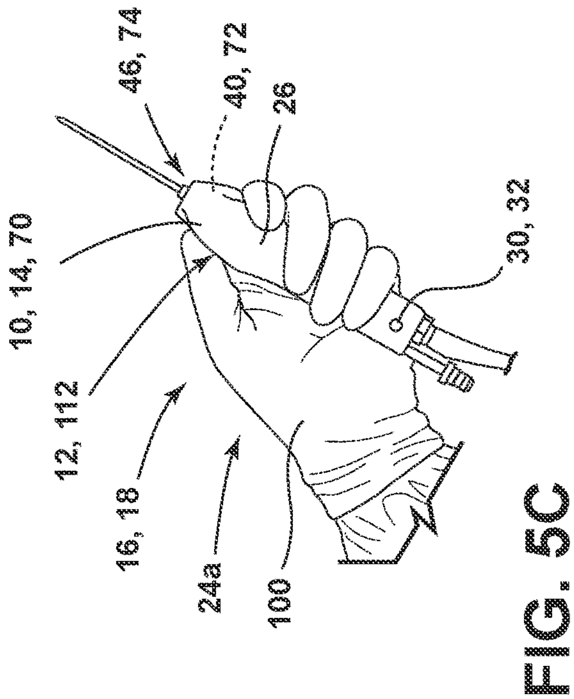
FIG. 5C is a pictorial representation of the surgical device demonstrated in FIGS. 5A-5B molded to accommodate a first grip.
Figure 5A:
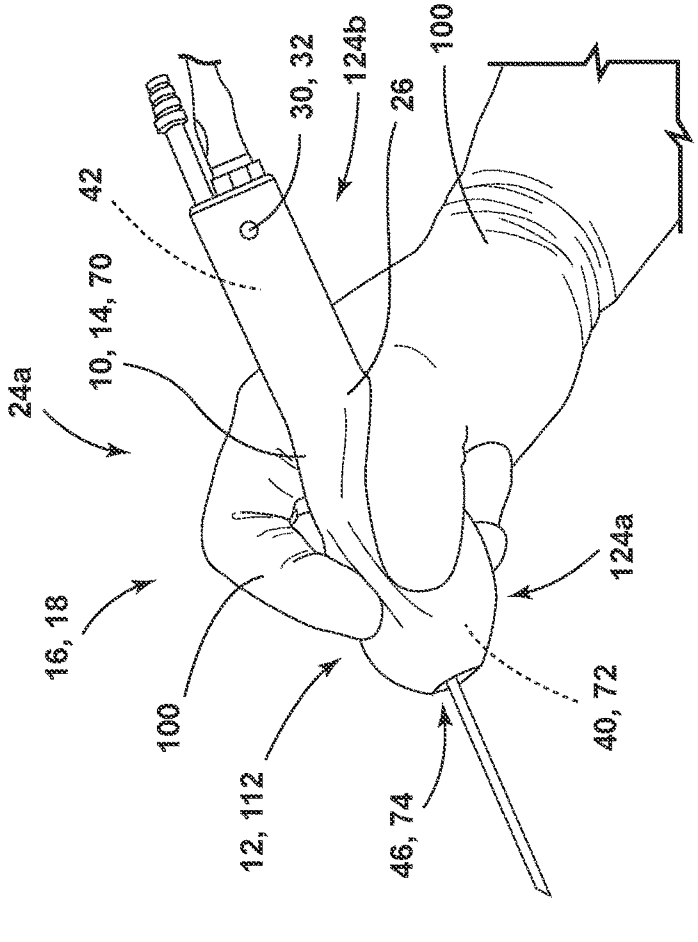
FIG. 5A is a pictorial view of a surgical device implemented via a tripod or pencil-grip having a right-handedness.

Referring now to FIGS. 5A-5C, a surgical device 16 is demonstrated comprising the handle portion 12 with the moldable grip 14 customized in various jammed conditions 24*a* to accommodate different dexterities and gripping styles with the same surgical device 16. As shown in FIG. 5A, the contoured profile 102 of the moldable grip 14 is demonstrated in the jammed condition conforming to a right-handed user implementing a pencil or tripod grip. FIG. 5B demonstrates the contoured profile 102 molded to accommodate a left-handed user implementing a pencil grip. FIG. 5C demonstrates the hand 100 of the user engaging the moldable grip 14 of the handle portion 12 in a first grip. In each case, the jamming material 20 of the handle portion 12 may be molded or manipulated in the flexible condition 24*b* by releasing a vacuum pressure condition of the enclosed cavity 22, such that the jamming material 20 can be flexibly manipulated by engaging and applying pressure to the external engagement layer 26. Once the jamming material 20 is molded to the desired exterior contour profile 102, the moldable grip 14 may be adjusted to the jammed condition 24*a* by evacuating air pressure from within the enclosed cavity 22. In this way, the moldable grip 14 may be customized to suit different handedness of the user as well as a variety of gripping styles. Such customization may improve the comfort of users, thereby improving the user experience and, further, the control of the surgical device 16 which may improve procedural success.

Figure 6A:
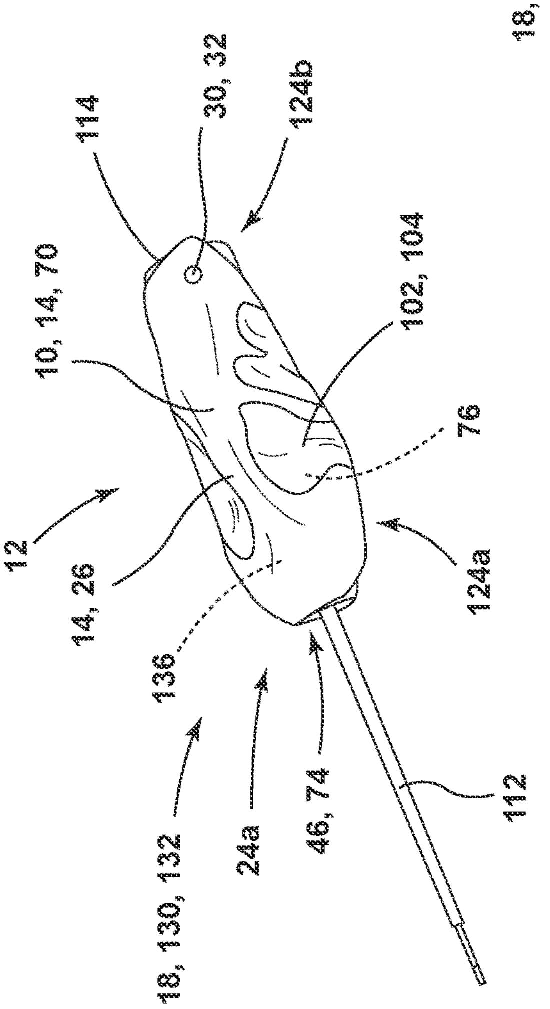
FIG. 6A demonstrates a pictorial diagram of an exemplary surgical instrument comprising a moldable grip.
Figure 6B:
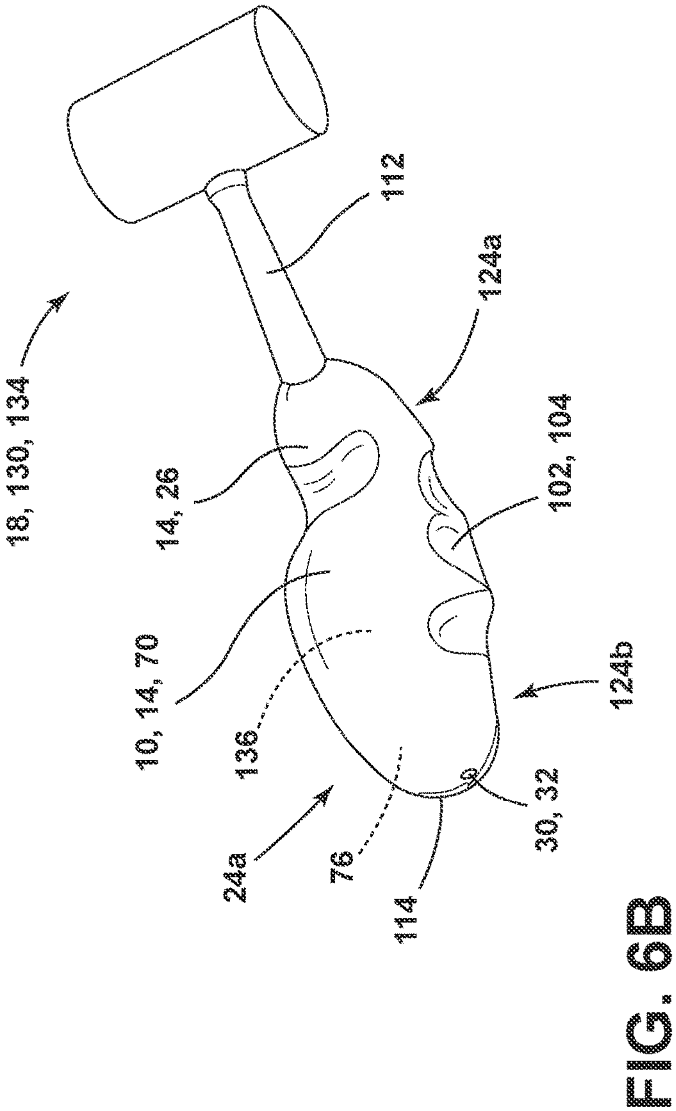
FIG. 6B demonstrates a pictorial diagram of an exemplary surgical instrument comprising a moldable grip.

Referring now to FIGS. 6A and 6B, the handle apparatus 10 is demonstrated in reference to exemplary handheld tools 130. As previously discussed, the handle apparatus 10 may be utilized to accommodate the handedness and grip style of a user in reference to a variety of the surgical implements 18, including handheld tools 130 and similar devices. As shown in FIG. 6A, the handle portion 12, comprising the moldable grip 14, is shown implemented in connection with the tool body 112 of a screwdriver 132. The moldable grip 14 is shown in the jammed condition 24*a* comprising the exterior profile 102 formed to a pincer-style grip that may be implemented for fine screw-driving applications requiring detailed manipulation of the handheld tool 130. As similarly discussed in reference to the exemplary surgical devices 16, the moldable grip 14 comprises the valve 30 and valve aperture 32, which may be selectively connected to the pump 34 to transition the jamming material 20 disposed in the enclosed cavity 22 from the jammed condition 24*a* to the flexible condition 24*b*. In this way, the moldable grip 14 may be implemented to provide a customized grip for the handheld tool 130 in the form of the screwdriver 132.

As demonstrated in FIG. 6B, the handle portion 12 comprising the moldable grip 14 is implemented in connection with the tool body 112 of a mallet 134. In this example, the exterior contoured profile 102 of the moldable grip 14 is molded to conform to a fixed grip extending over a shank 136 of the mallet 134. The shank 136 may be similar to the support post 110 in providing a structural connection of the handle apparatus 10 to the tool body 112 of the mallet 134. The engagement interface 104 of the moldable grip 14 is shown customized to suit a first or cylindrical grip of a user having a left-handedness. In this configuration, the moldable grip 14 may provide for improved comfort and control associated with the use of the handheld tool 130 in the form of mallet 134.

Figure 7B:
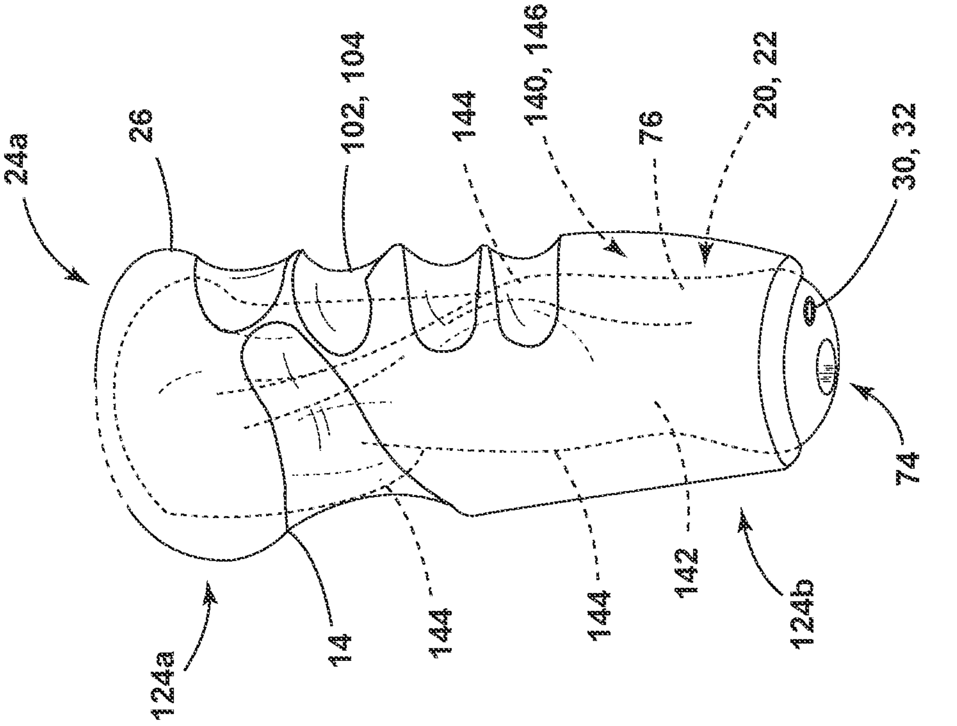
FIG. 7B is a pictorial diagram demonstrating the moldable grip of FIG. 7A, demonstrating the moldable grip in a custom modified configuration and affixed in a jammed condition.
Figure 7A:
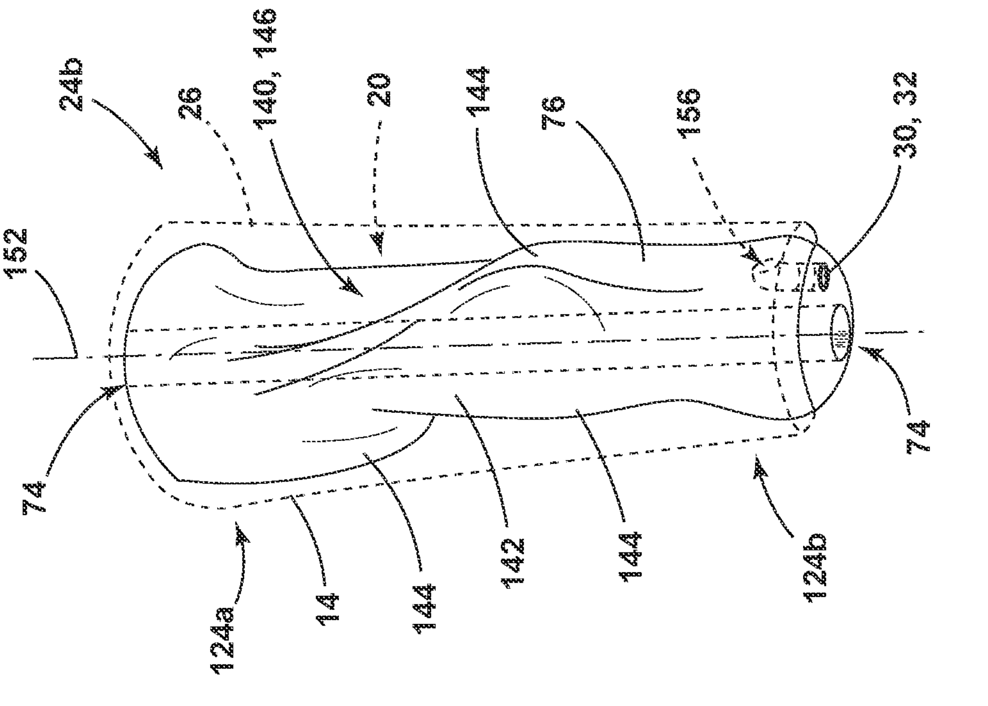
FIG. 7A is a partially hidden view of a handle portion comprising a moldable grip having a rigid interior shell providing a plurality of surface contours to which the moldable grip conforms in a molded configuration.

Referring now to FIGS. 7A and 7B, in some implementations, the handle apparatus 10 may comprise a contoured core 140 formed by a rigid structure 142 that may incorporate one or more structural surface contours 144 over an exterior core surface 146. The exterior core surface 146 may be disposed within the moldable grip 14 between the receiving opening 74 and the engagement layer 26. In this configuration, the contoured core 140 may provide for the rigid structure 142 over which the jamming material 20 may necessarily conform in response to an exterior pressure or force applied by the user to the engagement layer 26. In this way, the surface contours 144 of the moldable grip 14 may provide for one or more fixed or permanent grip features that may be customized by forming the jamming material 20 over the rigid structure 142 within the engagement layer 26.

As shown in FIG. 7A, the jamming material 20 and the engagement layer 26 are shown as broken lines extending over the contoured core 140. In the example shown, the exterior core surface 146 of the contoured core 140 comprises a plurality of structural surface contours 144, which may correspond to one or more ergonomic features or structural lever arms that may assist in the operation of the surgical implement to which the handle apparatus 10 is applied. For example, the rigid structure 142 of the structural surface contours 144 may extend away from a support axis 152 of the support post 110. In this configuration, the structural surface contour 144 may provide a lever arm or a mechanical advantage assisting in a rotation about the support axis 152 to improve the operation of the handle apparatus 10 with a specific surgical implement. Additionally, the structural surface contours 144 may provide for one or more surface features over which the exterior contoured profile 102 and the resulting customized engagement interface 104 may be molded to conform to a variety of ergonomic shapes. As discussed throughout the disclosure, the various shapes of the moldable grip 14 may be customized to suit one or more gripping styles associated with the corresponding surgical implement. In this way, the handle apparatus 10 may provide for a hybrid between a preconfigured rigid structure 142 that may provide the benefit of a structurally or ergonomically beneficial surface contour 144 while also providing the customized engaging surface contour 144 facilitated by the jamming material 20 of the moldable grip 14.

In FIG. 7B, the moldable grip 14 is shown in the jammed condition 24*a* with the external engagement layer 26 molded to conform to a left-handed first grip. As shown, the structural surface contours 144 of the contoured core 140 are demonstrated as broken lines and the engagement layer 26 is shown as a solid line for clarity. FIG. 7B demonstrates the relationship between the exterior contoured profile 102 formed by the engagement layer 26 conforming to the jamming material 20 extending over the exterior core surface 146 of the contoured core 140. In particular, the depth of the jamming material 20 between the engagement layer 26 and the contoured core 140 may vary based on the contours formed over the engagement layer 26 as well as the structural surface contours 144 of the rigid structure 142 forming the contoured core 140. In this configuration, the shape or form of the exterior core surface 146 may serve as a rigid or semi-rigid template over which the customized engagement interface 104 is formed.

FIGS. 7A and 7B further demonstrate a fluid connection path corresponding to the valve aperture 32 that extends through the rigid structure 142 of the contoured core 140. In such cases, the valve 30 and valve aperture 32 may be formed as an interior passage 156 extending through the rigid structure 142 and into the enclosed cavity 22 between the interior liner 76 and the external engagement layer 26. In this way, the rigid structure 142 provided by the contoured core 140 may define the interior passage 156 to accommodate the valve 30 and valve aperture 32 as demonstrated in FIG. 7A. Though demonstrated in reference to the contoured core 140, it shall be understood that the interior liner 76 may be implemented similarly with the rigid structure 142 to provide an adequate thickness through which the interior passage 156 may extend to suit a variety of handle apparatuses 10. Accordingly, the valve 30 and/or the valve aperture 32 may be implemented in the handle apparatus 10 in various implementations and variations without requiring the structural surface contours 144 associated with the contoured core 140. Stated otherwise, the contoured core 140 may more generally correspond to a core that may correspond to the interior liner 76 formed from the rigid structure 142 having a smooth exterior surface that may conform to various shapes, sizes, and/or proportions.

In some implementations, a surgical device comprises a support member forming a connection interface extending from a portion of the surgical device. A moldable handle comprises an interior liner extending over at least a portion of the connection interface and an exterior engagement layer in connection with the interior liner and defining a grip surface. The interior liner and the exterior engagement layer form an enclosed cavity therebetween and a jamming material is disposed in the enclosed cavity.

In various implementations, the systems and methods described in the application may comprise one or more of the following features or steps alone or in combination:

the jamming material is controlled between a jammed condition and a flexible condition in response to a variation in pressure within the enclosed cavity;

a valve in connection with an aperture formed in the moldable handle, wherein the valve regulates the pressure by restricting airflow from the enclosed cavity to a local environment proximate to the surgical device;

the jammed condition positionally binds particles forming the jamming material to one another by closing interstitial spaces therebetween, thereby forming a rigid body in the jammed condition retaining a shape of the jamming material as molded in the flexible condition;

the exterior engagement layer is an impermeable, flexible membrane that conforms to a shape of the jamming material;

the interior liner comprises a rigid shell comprising a receiving opening complementary to an exterior profile of the support member;

the interior liner is structurally connected to the support member of the surgical device in a fixed arrangement in an assembled configuration;

the rigid shell forms a contoured core defining a plurality of surface contours to which the jamming material and the exterior engagement surface conform in response to a compression of the exterior engagement surface;

the contoured core forms a surface over which the membrane and the jamming material is molded in response to pressure applied to the grip surface;

the rigid shell comprises an exterior engagement layer forming at least one contoured surfaces;

the exterior engagement layer of the rigid shell is a compression form over which the jamming material and the exterior engagement layer are molded;

the exterior engagement layer of the rigid shell forms a rigid (or semi-rigid) molding form over which the jamming material and the exterior engagement layer are formed;

a fluid pump fluidically connected to the enclosed cavity, wherein the fluid pump is selectively activated to control the pressure from the jammed condition to the flexible condition;

the fluid pump is selectively connected to a drive motor of the surgical device via a decoupling assembly;

the decoupling assembly comprises a switch in connection with a housing of the surgical device, wherein a movement of the switch selectively engages a decoupling gear to a drive gear of the drive motor;

a retention plate that engages a distal end portion of the support member, wherein the retention plate retains the moldable handle on the support member between a body of the surgical device and the retention plate; and/or the retention plate is a portion of a battery housing that removably engages the support member.

In some implementations, a method for providing a handle portion of a surgical instrument is disclosed. The method comprises engaging a support member of the surgical device in connection with an interior liner of a handle portion. The interior liner is connected to an exterior engagement layer forming an enclosed cavity therebetween. The method further includes applying pressure to the exterior engagement layer in connection with the interior liner in a flexible condition, thereby molding a jamming material within the enclosed cavity into a contoured surface to which the exterior engagement layer conforms. The air pressure is removed from within the enclosed cavity, thereby restricting a relative movement of particles forming the jamming material in a jammed condition.

In various implementations, the systems and methods described in the application may comprise one or more of the following features or steps alone or in combination:

applying the pressure comprises gripping the exterior engagement surface;

selectively removing the handle portion from the support member by slidably disengaging the handle portion from the interior liner;

supplying air pressure into the enclosed cavity, thereby allowing the relative movement of particles and transitioning the jamming material to the flexible condition;

applying the pressure defines a handedness of one or more features formed by the jamming material of the handle portion;

the handedness comprises a left handedness or a right handedness;

applying the pressure defines a grip style of the handle, wherein the grip style comprises at least one of a first grip, a digital pronate grip, a pincer grip, and a tripod grip; and/or the surgical instrument is a power tool comprising a drive motor and the removing air pressure from the enclosed cavity comprises selectively engaging the drive motor with a pump of the surgical instrument.

In some implementations, a powered surgical device comprises a support member forming a connection interface extending from a portion of the surgical device. A user interface is configured to activate a control signal of the powered surgical device. The device includes a moldable handle comprising an interior liner extending over at least a portion of the connection interface and an exterior engagement layer in connection with the interior liner. The exterior engagement layer defines a grip surface, and the interior liner and the exterior engagement layer form an enclosed cavity therebetween. An opening is formed through the interior liner and the exterior engagement layer through which the user interface is exposed. A jamming material is disposed in the enclosed cavity. The jamming material is transitioned between a jammed condition and a flexible condition in response to a variation in pressure within the enclosed cavity.

It will be understood that any described processes or steps within described processes may be combined with other disclosed processes or steps to form structures within the scope of the present device. The exemplary structures and processes disclosed herein are for illustrative purposes and are not to be construed as limiting.

It is also to be understood that variations and modifications can be made on the aforementioned structures and methods without departing from the concepts of the present device, and further it is to be understood that such concepts are intended to be covered by the following claims unless these claims by their language expressly state otherwise.

The above description is considered that of the illustrated embodiments only. Modifications of the device will occur to those skilled in the art and to those who make or use the device. Therefore, it is understood that the embodiments shown in the drawings and described above are merely for illustrative purposes and not intended to limit the scope of the device, which is defined by the following claims as interpreted according to the principles of patent law, including the Doctrine of Equivalents

The invention claimed is:

1. A surgical device comprising:

a support member forming a connection interface extending from a portion of the surgical device;

a moldable handle comprising:

an interior liner extending over at least a portion of the connection interface;

an exterior engagement layer in connection with the interior liner and defining a grip surface, wherein the interior liner and the exterior engagement layer form an enclosed cavity therebetween; and a jamming material disposed in the enclosed cavity, wherein the jamming material is controlled between a jammed condition and a flexible condition in response to a variation in a pressure within the enclosed cavity, and the jammed condition positionally binds particles forming the jamming material to one another by closing interstitial spaces therebetween, thereby forming a rigid body in the jammed condition retaining a shape of the jamming material as molded in the flexible condition.

2. The surgical device according to claim 1, further comprising:

a valve in connection with an aperture formed in the moldable handle, wherein the valve regulates the pressure by restricting airflow from the enclosed cavity to a local environment proximate to the surgical device.

3. The surgical device according to claim 1, wherein the exterior engagement layer is an impermeable, flexible membrane that conforms to a shape of the jamming material.

4. The surgical device according to claim 1, wherein the interior liner comprises a rigid shell comprising a receiving opening complementary to an exterior profile of the support member.

5. The surgical device according to claim 4, wherein the interior liner is structurally connected to the support member of the surgical device in a fixed arrangement in an assembled configuration.

6. The surgical device according to claim 4, wherein the rigid shell forms a contoured core defining a plurality of surface contours to which the jamming material and the exterior engagement surface conform in response to a compression of the exterior engagement surface.

7. The surgical device according to claim 1, further comprising:

a fluid pump fluidically connected to the enclosed cavity, wherein the fluid pump is selectively activated to control the pressure from the jammed condition to the flexible condition.

8. The surgical device according to claim 7, wherein the fluid pump is selectively connected to a drive motor of the surgical device via a decoupling assembly.

9. The surgical device according to claim 8, wherein the decoupling assembly comprises a switch in connection with a housing of the surgical device, wherein a movement of the switch selectively engages a decoupling gear to a drive gear of the drive motor.

10. The surgical device according to claim 1, further comprising:

a retention plate that engages a distal end portion of the support member, wherein the retention plate retains the moldable handle on the support member between a body of the surgical device and the retention plate.

11. A method for providing a handle portion of a surgical device, the method comprising:

engaging a support member of the surgical device in connection with an interior liner of a handle portion, wherein the interior liner is connected to an exterior engagement layer forming an enclosed cavity therebetween;

applying a molding force to the exterior engagement layer in connection with the interior liner in a flexible condition, thereby molding a jamming material within the enclosed cavity into a contoured surface to which the exterior engagement layer conforms;

evacuating air from the enclosed cavity, thereby restricting a relative movement of particles forming the jamming material in a jammed condition, wherein the jamming material is controlled between a jammed condition and a flexible condition in response to a variation in a pressure within the enclosed cavity; and regulating the pressure by restricting airflow from the enclosed cavity to a local environment proximate to the surgical device with a valve in connection with an aperture formed in the interior liner.

12. The method according to claim 11, further comprising:

selectively removing the handle portion from the support member by slidably disengaging the handle portion from the interior liner.

13. The method according to claim 11, further comprising:

supplying air into the enclosed cavity, thereby allowing the relative movement of particles and transitioning the jamming material to the flexible condition.

14. The method according to claim 11, wherein applying the molding force defines a handedness of one or more features formed by the jamming material of the handle portion.

15. The method according to claim 14, wherein the handedness comprises a left handedness or a right handedness.

16. The method according to claim 11, wherein applying the molding force defines a grip style of the handle, wherein the grip style comprises at least one of a first grip, a digital pronate grip, a pincer grip, and a tripod grip.

17. The method according to claim 11, wherein the surgical instrument is a power tool comprising a drive motor and evacuating air from the enclosed cavity comprises selectively engaging the drive motor with a pump of the surgical instrument.

18. A powered surgical device comprising:

a support member forming a connection interface extending from a portion of the surgical device;

a user interface configured to activate a control signal of the powered surgical device; and a moldable handle comprising:

an interior liner extending over at least a portion of the connection interface;

an exterior engagement layer in connection with the interior liner and defining a grip surface, wherein the interior liner and the exterior engagement layer form an enclosed cavity therebetween;

an opening formed through the interior liner and the exterior engagement layer, wherein the user interface is exposed through the opening; and a jamming material disposed in the enclosed cavity, wherein the jamming material is transitioned between a jammed condition and a flexible condition in response to a variation in a pressure within the enclosed cavity, wherein the jammed condition positionally binds particles forming the jamming material by closing interstitial spaces therebetween, thereby forming a rigid body in the jammed condition retaining a shape of the jamming material as molded in the flexible condition.

* * * * *